United States Patent [19]
Kabanov et al.

[11] Patent Number: 6,153,193
[45] Date of Patent: Nov. 28, 2000

[54] COMPOSITIONS FOR TARGETING BIOLOGICAL AGENTS

[75] Inventors: Alexander V. Kabanov, Omaha, Nebr.; Valery Yu. Alakhov, Quebec, Canada; Vladimir P. Chekhonin, Moscow, Russian Federation; Elena V. Batrakova, Moscow, Russian Federation; Victor A. Kabanov, Moscow, Russian Federation

[73] Assignee: Supratek Pharma Inc., Canada

[21] Appl. No.: 08/478,979

[22] Filed: Jun. 7, 1995

Related U.S. Application Data

[63] Continuation-in-part of application No. 08/054,403, Apr. 28, 1993, abandoned.

[51] Int. Cl.$^7$ ..................................................... A61K 38/17
[52] U.S. Cl. ..................................... 424/184.1; 424/178.1; 514/772.1
[58] Field of Search ............................. 424/184.1, 178.1; 514/772.1

[56] References Cited

U.S. PATENT DOCUMENTS

| | | |
|---|---|---|
| 4,027,013 | 5/1977 | Bick et al. . |
| 4,188,373 | 2/1980 | Krezanoski . |
| 4,474,752 | 10/1984 | Haslam et al. . |
| 4,609,546 | 9/1986 | Hiratani . |
| 4,740,498 | 4/1988 | Hirao et al. . |
| 4,772,466 | 9/1988 | Alison et al. . |
| 4,801,452 | 1/1989 | Hunter et al. . |
| 4,837,014 | 6/1989 | Hunter et al. . |
| 4,865,835 | 9/1989 | Begent . |
| 4,873,083 | 10/1989 | Hunter et al. . |
| 4,879,109 | 11/1989 | Hunter . |
| 4,882,168 | 11/1989 | Casey et al. . |
| 4,897,263 | 1/1990 | Hunter . |
| 4,937,070 | 6/1990 | Hunter . |
| 4,957,735 | 9/1990 | Huang ..................................... 424/85.8 |
| 4,997,644 | 3/1991 | Hunter . |
| 5,017,370 | 5/1991 | Hunter et al. . |
| 5,028,599 | 7/1991 | Hunter . |
| 5,030,448 | 7/1991 | Hunter . |
| 5,032,394 | 7/1991 | Hunter . |
| 5,039,520 | 8/1991 | Hunter . |
| 5,041,288 | 8/1991 | Hunter . |
| 5,047,236 | 9/1991 | Hunter et al. . |
| 5,064,643 | 11/1991 | Hunter et al. . |
| 5,071,649 | 12/1991 | Hunter . |
| 5,078,995 | 1/1992 | Hunter et al. . |
| 5,080,894 | 1/1992 | Hunter et al. . |
| 5,089,260 | 2/1992 | Hunter et al. . |
| 5,114,708 | 5/1992 | Hunter et al. . |
| 5,152,979 | 10/1992 | Hunter . |
| 5,182,106 | 1/1993 | Mezrow et al. . |
| 5,183,687 | 2/1993 | Hunter et al. . |
| 5,198,211 | 3/1993 | Hunter et al. . |
| 5,234,683 | 8/1993 | Hunter et al. . |
| 5,240,701 | 8/1993 | Hunter et al. . |
| 5,240,702 | 8/1993 | Hunter et al. . |
| 5,250,294 | 10/1993 | Hunter et al. . |
| 5,412,072 | 5/1995 | Sakurai et al. . |
| 5,417,982 | 5/1995 | Modi . |
| 5,436,170 | 7/1995 | Cornell et al. ......................... 436/527 |
| 5,449,513 | 9/1995 | Yokoyama et al. .................. 424/78.08 |
| 5,466,445 | 11/1995 | Hunter . |
| 5,470,568 | 11/1995 | Lee . |
| 5,488,034 | 1/1996 | McGregor et al. . |
| 5,494,660 | 2/1996 | Hunter et al. . |
| 5,523,492 | 6/1996 | Emanuele et al. . |
| 5,531,925 | 7/1996 | Landh et al. . |
| 5,554,372 | 9/1996 | Hunter . |
| 5,567,859 | 10/1996 | Emanuele et al. . |
| 5,573,934 | 11/1996 | Hubbel et al. . |
| 5,591,715 | 1/1997 | Coon et al. . |
| 5,622,649 | 4/1997 | Hunter et al. . |
| 5,648,071 | 7/1997 | Hunter et al. . |
| 5,656,611 | 8/1997 | Kabanov et al. . |
| 5,674,911 | 10/1997 | Emanuele et al. . |
| 5,691,387 | 11/1997 | Emanuele et al. . |
| 5,696,090 | 12/1997 | McGregor et al. . |
| 5,696,298 | 12/1997 | Emanuele et al. . |
| 5,698,529 | 12/1997 | Alakhov et al. . |
| 5,776,891 | 7/1998 | Coon et al. . |
| 5,840,319 | 11/1998 | Alakhov et al. . |
| 5,885,590 | 3/1999 | Hunter et al. . |
| 6,040,295 | 2/2000 | Rolland et al. . |

FOREIGN PATENT DOCUMENTS

| | | |
|---|---|---|
| 0211601 | 2/1997 | European Pat. Off. . |
| WO 86/.07539 | 12/1986 | WIPO . |
| WO 88/01873 | 3/1988 | WIPO . |
| WO 88/06038 | 8/1988 | WIPO . |
| WO89/00812 | 2/1989 | WIPO . |
| WO 91/16058 | 10/1991 | WIPO . |
| WO 92/00101 | 1/1992 | WIPO . |
| WO 92/16484 | 10/1992 | WIPO . |
| WO94/08564 | 4/1994 | WIPO . |
| WO95/03829 | 2/1995 | WIPO . |
| WO96/00801 | 7/1996 | WIPO . |
| WO96/40056 | 12/1996 | WIPO . |
| WO99/39731 | 8/1999 | WIPO . |

OTHER PUBLICATIONS

Kabanov et al., The neuroleptic activity of haloperidol increases after its solubilization in surfactant micelles. FEBS Letters 258(2):343–345, 1989.

Chekhonin et al., Fatty acid acylated Fab–fragments of antibodies to neurospecific proteins as carriers for neuroleptic targeted delivery in brain. FEBS Letters 287(1,2);149–152, 1991.

Kabanov et al., A new class of drug carriers: micelles of poly(oxyethylene)–poly(oxypropylene) block copolymers as microcontainers for drug targeting from blood in brain. Journal of Controlled Release 22:141–157, 1992.

(List continued on next page.)

*Primary Examiner*—Donna C. Wortman
*Attorney, Agent, or Firm*—Mathews, Collins, Shepherd & Gould, P.A.

[57] ABSTRACT

Improved pharmaceutical compositions useful in targeting biological agents to particular tissue and compositions useful for administering biological agents to the brain.

35 Claims, 1 Drawing Sheet

OTHER PUBLICATIONS

Budavari et al., Eds., *The Merck Index*, Eleventh Edition, Merck & Co., Rahway, NJ, 1989, p. 712.

Chekhonin et al., "Fatty Acid Acylated Fab–Fragments Of Antibodies To Neurospecific Proteins As Carriers For Neuroleptic Targeted Delivery In Brain", *FEBS Lett.*, 287, N 1,2, 149–152 (1991).

Kabanov et al., "The Neuroleptic Activity Of Haloperidol Increases After Its Solubilization In Surfactant Micelles: Micelles As Microcontainers For Drug Targeting", *FEBS Lett.*, 258, N 2, 343–345 (1989).

Kabanov et al., "A New Class of Drug Carriers: Micelles of Poly(oxyethylene)—Poly(oxypropylene) Block Copolymers As Microcontainers For Drug Targeting From Blood In Brain", *J. Contr. Release*, 22, 141–158 (1992).

Kabanov et al., "Enhancement Of Macromolecule Penetration Into Cells And Nontraditional Drug Delivery Systems", *Sov. Sci. Rev. D. Physiochem. Biol.* (V.P. Skulachev ed.), vol. 11, Glasgow: Harwood Academic Publishers, part 2, pp. 1–77 (1992).

Kabanov et al., "Site Specific Drug Targeting", *CPhI '92 Conference Proceedings*, London: Eyre & Spotiswoode Ltd., pp. 89–96 (1993).

Kabanov et al., Polymeric Surfactant Micelles As Microcontainers . . . , *Journal of Neuroimmuno.* (Suppl 1): 130 (1991).

Chawla et al., "Aggregation of Insulin, Containing Surfactants, in Contact with Different Materials," Diabetes. vol. 34: 420–424 (1995).

Kabanov et al., "Interpolyelectrolyte and Block Ionomer Complexes for Gene Delivery: Physicochemical Aspects," Advanced Drug Delivery Reviews, Elsevier, vol. 30: 49–60 (1998).

Batrakova, "Effects of Pluronic Block Copolymers on Drug Absorption in Caco–2 Cell Monolayers," Pharmaceutical Research, vol. 15, No. 6, (1998).

Abstract, Database WPI Week 9519, Derwent Publ. Ltd. AN 95–144714 High Water Soluble Antitumour Adriamycin Agent Comprise Micellar Complex Block Copolymer Polyethyene Glycol Poly Amino acid.

Kataoka et al., "Block Copolymer Micelles As Vehicles for Drug Delivery," *Journal of Controlled Release*, vol. 24: 119–132 (1993).

COMPOSITIONS FOR TARGETING BIOLOGICAL AGENTS

This application is a continuation-in-part of U.S. application Ser. No. 08/054,403, filed Apr. 28, 1993 now abandoned.

The present invention relates to improvements in pharmaceutical compositions for use in targeting biological agents to a particular tissue and to compositions that are useful for administering biological agents to the brain.

The brain is isolated from circulatory blood because the endothelial cell lining of blood vessels in the brain is more selective than it is in other parts of the body with respect to the molecules that are allowed to diffuse into the interstitial space of the brain. The mechanism that isolates the brain is often referred to as a "blood-brain barrier." As a result of the blood-brain barrier, biological agents that are intended to affect the brain or a disease in the brain often must be administered in high dosage to compensate for the diffusion barrier provided by the blood-brain barrier. Animals to whom the high doses are administered are at greater risk of experiencing toxic or other side effects. It is therefore desirable to enhance the permeability of chemotherapeutic agents across the blood-brain barrier. See, Goodman's and Gilman's *The Pharmacological Basis of Therapeutics*, Eighth Edition, p. 11.

In the brain and in other tissues it is often desirable to target a biological agent to a particular tissue at which the agent is anticipated to beneficially act. This desirability is particularly true for chemotherapeutic agents that potentially have highly toxic effects on non-target tissues. For instance, most anti-cancer chemotherapeutic agents function by selectively poisoning replicating cells. This mechanism inevitably targets the rapidly replicating cells, such as those of the bone marrow that generate a number of important blood cells. If the biodistribution of the chemotherapeutic drug is changed so that useful concentrations are maintained in the cancerous tissue or the tissue in which the cancer resides while concentrations distal from the cancer situs are reduced, the scope of toxic side effects will generally be reduced.

Additionally, since cancer, antimicrobial and other biological agents exhibit toxicities, it would be beneficial if dosages were lowered without adversely affecting the therapeutic index.

Tumors of the central nervous system present a particularly difficult therapeutic challenge. Such tumors are often difficult to surgically excise and surgical excision can have unacceptable consequences. These tumors can be difficult to treat with radiation since they are sometimes difficult to precisely locate and are often too close to tissues that are critical to the well-being of the tumor patient. Such tumors cannot be effectively treated by standard chemotherapies since the fraction of the administered chemotherapeutic agent that will reach the tumor is very small. The effective dosage at the tumor cannot be increased by administering higher dosages to the patient, since standard dosages are generally close to the dose that cause unacceptable side effects.

SUMMARY OF THE INVENTION

In one embodiment, the invention provides a pharmaceutical composition comprising:

(a) an biological agent;

(b) a polyether block copolymer comprising an A-type linear polymeric segment joined at one end to a B-type linear polymeric segment, wherein the A-type segment is of relatively hydrophilic character, the repeating units of which contribute an average Hansch-Leo fragmental constant of about −0.4 or less and have molecular weight contributions between about 30 and about 500, wherein the B-type segment is of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; and (c) a targeting moiety coupled to a lipophilic moiety comprising a hydrocarbon having from about 3 to about 41 carbon atoms, more preferably a hydrocarbon having from about 5 to about 25 carbon atoms, yet more preferably, a hydrocarbon having from about 9 to about 17 carbon atoms.

In a preferred first embodiment, the polyether block copolymer is selected from the group consisting of polymers of formulas $$A\text{-}B\text{-}A', \quad (I)$$

$$A\text{-}B, \quad (II)$$

$$B\text{-}A\text{-}B', \quad (III)$$

or $$L(R^1)(R^2)(R^3)(R^4) \quad (IV)$$

wherein A and A' are A-type linear polymeric segments, B and B' are B-type linear polymeric segments, and $R^1$, $R^2$, $R^3$ and $R^4$ are either block copolymers of formulas (I), (II) or (III) or hydrogen and L is a linking group, with the proviso that no more than two of $R^1$, $R^2$, $R^3$ or $R^4$ shall be hydrogen.

In a preferred embodiment, the composition is adapted to include micelles composed of the block copolymer or to form micelles composed of the block copolymers during the course of administration or subsequent thereto. Preferably, at least about 0.1% of the biological agent is incorporated in the micelles, more preferably, at least about 1% of the biological agent, yet more preferably, at least about 5% of the biological agent.

In a preferred embodiment, the hydrophobe percentage of the copolymer of the composition is at least about 50% more preferably, at least about 60%, yet more preferably 70%.

In another preferred embodiment, the hydrophobe weight of the copolymer is at least about 900, more preferably, at least about 1700, yet more preferably at least about 2000, still more preferably at least about 2300.

In further preferred embodiments, the hydrophobe weight is at least about 2000 and the hydrophobe percentage is at least about 20%, preferably 35%; or the hydrophobe weight is at least about 2300 and the hydrophobe percentage is at least about 20%, preferably 35%.

In yet another preferred embodiment, the copolymer or copolymers of the composition have a critical micellar concentration ("CMC") of no more than about 0.5% wt/vol at 37° C. in an isotonic aqueous solution, preferably, no more than about 0.05% wt/vol, more preferably, no more than about 0.01% wt/vol, yet more preferably, no more than about 0.003% wt/vol.

Preferably, the copolymers of the composition conform to Formula (V), which is set forth in the text below. Particularly preferred among these copolymers are those having hydrophobe weights between about 1500 and about 2000, preferably between about 1710 and about 1780, and hydrophobe percentages between about 85% and about 95%, preferably between about 88% and about 92%. Also particularly preferred among these copolymers are those having hydrophobe weights between about 3000 and about 3500, preferably between about 3200 and about 3300, and hydrophobe percentages between about 15% and about 25%, preferably between about 18% and about 22%. Additionally particularly preferred among these polymers are that having hydrophobe weights between about 3500 and about 4000, preferably between about 3700 and about 3800, and hydrophobe percentages between about 25% and about 35%, preferably between about 28% and about 32%.

In a preferred embodiment, the biological agent of the composition is an agent that affects the function of the brain or treats or prevents a disease of the brain.

In a second embodiment, the invention provides a pharmaceutical composition comprising an biological agent solubilized in polymeric micelles having associated therewith a targeting moiety coupled to a lipophilic moiety comprising hydrocarbon having from about 3 to about 41 carbon atoms, more preferably a hydrocarbon having from about 5 to about 25 carbon atoms, yet more preferably, a hydrocarbon having from about 9 to about 17 carbon atoms.

In another embodiment, the invention provides a method of targeting a biological agent to a pre-selected tissue. The method comprises administering the composition described above, wherein the targeting moiety is selected to target the tissue, to an animal having the pre-selected tissue.

In yet another embodiment, the invention provides a method of treating a microbial disease or a tumor of the brain by administering a composition comprising:

(a) a chemotherapeutic agent; and (b) a polyether block copolymer comprising an A-type linear polymeric segment joined at one end to a B-type linear polymeric segment, wherein the A-type segment is of relatively hydrophilic character, the repeating units of which contribute an average Hansch-Leo fragmental constant of about −0.4 or less and have molecular weight contributions between about 30 and about 500, wherein the B-type segment is of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage. In a preferred embodiment, the composition used in this embodiment will include a targeting molecule.

DEFINITIONS

DETAILED DESCRIPTION

Figure 1A:
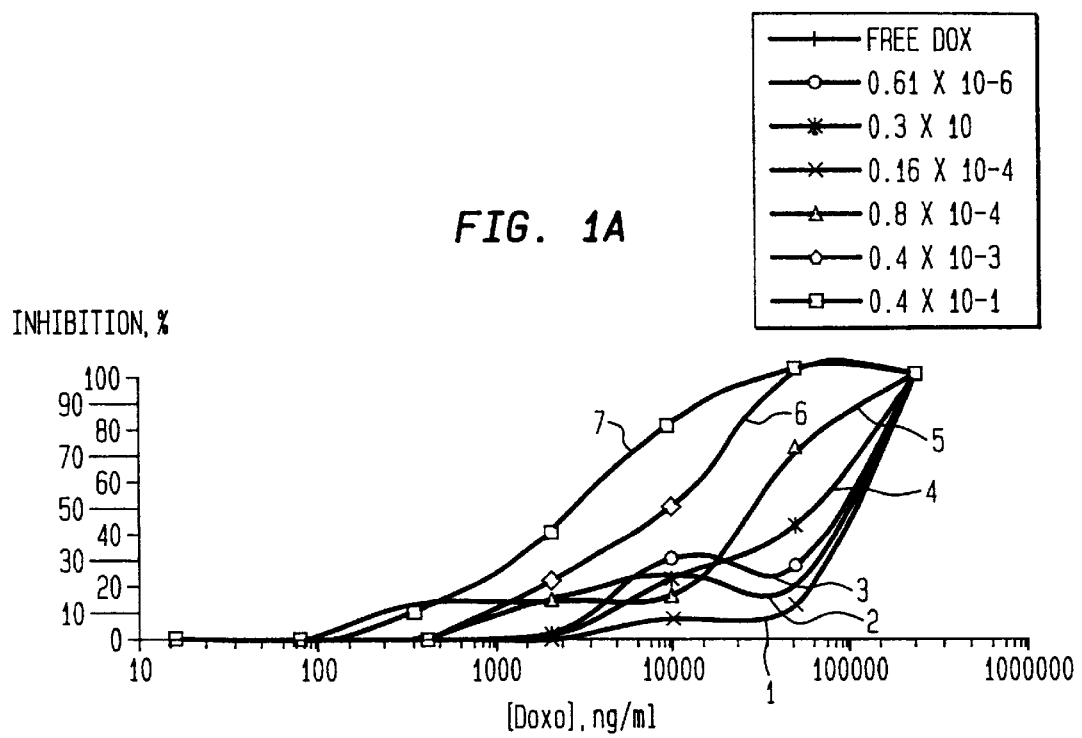
FIGS. 1A and 1B show the inhibition of doxorubicin-resistant MCF7 cells incubated with various concentrations of doxorubicin and PLURONIC® L61.

The terms or phrases listed below shall have the following meaning:

| | |
|---|---|
| biological agent | an agent that is useful for diagnosing or imaging or that can act on a cell, organ or organism, including but not limited to drugs (pharmaceuticals) to create a change in the functioning of the cell, organ or organism. Such agents can include but are not limited to nucleic acids, polynucleotides, antibacterial agents, antiviral agents, antifungal agents, anti-parasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds and local anesthetics. |
| central nervous system agents | biological agents that act on cells of the central nervous system or diseases of the central nervous system. |
| chemotherapeutic agent | a biological agent that inhibits the growth or decreases the survival of neoplastic or pathogenic microbial cells or inhibits the propagation (which includes without limitation replication, viral assembly or cellular infection) of a virus. |
| hydrophobe percentage | the percentage of the molecular weight of a block copolymer that is made up of B-type blocks. |
| hydrophobe weight | the molecular weight contribution of the B-type blocks of a block copolymer. |
| $IC_{50}$ | the concentration at which 50% cytotoxicity is obtained. Cytotoxicity can be measured by the method of Alley et al., Cancer Res. 48: 589–601, 1988 or Scudiero et al., Cancer Res., 48:4827, 1988. In particular, it can be measured based on the drug concentration at which a 50% reduction in the activity of mitochondrial enzymes is observed. |
| lipophilic moiety | a lipophilic substituent that is joined to a targeting moiety and that partitions into the lipophilic portion of copolymer micelles. |
| microbe | a bacteria, mycoplasma, yeast or fungi, virus or parasite (such as a malaria parasite). |
| targeting moiety | a molecular structure that is recognized by a cellular, tissue, viral or substratum component such as a cell-surface receptor or acceptor molecule. |

It will be understood that the copolymer characteristics described below are suitable for the compositions of both the targeting embodiments of the invention and the brain chemotherapy embodiments of the invention.

The mechanism by which the blood-brain barrier works is believed to be substantially similar to the mechanism by which many cells become resistant to the action of biological agents. Both mechanisms are believed to make use of the membrane pump proteins belonging to the glycoprotein P family of proteins. See, for example, Tatsuta et al., *J. Biol. Chem.* 267: 20383–20391, and Goldstein et al., *Cancer Treatment Res.* 57: 101–119. These pumps are believed to act by exporting biological agents that diffuse into a cell, such as the endothelial cells that line blood vessels in the brain. Recent observations described in more detail in U.S. application Ser. No. 08/478,978, entitled "Biological Agent Compositions,", filed concurrently herewith on Jun. 7, 1995, now U.S. Pat. No. 5,817,321 demonstrate the effectiveness of the block copolymers of the invention in enhancing the potency of chemotherapeutic drugs and reversing drug resistance is highly dependent (a) on the hydrophobe percentage and (b) on the hydrophobe weight. The effectiveness increases with either an increase in the percentage (a) or an increase in weight (b), or both. These hydrophobe percentage and hydrophobe weight increases also correlate with improved micelle formation properties wherein micelle formation for these copolymers occurs at lower concentrations. See, Hurter et al., *Macromolecules* 26: 5030, 1993; Hurter et al., *Macromolecules* 26: 5592, 1993; Alexandris et al.,

*Macromolecules* 27: 2414, 1994. While not wishing to be limited to a particular theory, it is believed that micelle formation serves as a surrogate for measuring the physical properties that lead to improved biological agent delivery properties.

If, using doxorubicin as a model biological agent, the ratio of (a) the $IC_{50}$ (a measure of effective cytotoxicity concentration) for a copolymer-containing composition to (b) the $IC_{50}$ for free doxorubicin is plotted against the concentration of copolymer, the plot is biphasic, with a rapid decrease in the ratio seen as copolymer concentrations increase but remain under the CMC of the copolymer. Above the CMC, a rapid leveling off of the ratio is observed. See FIG. 1A. Maximal enhancement of biological agent activity occurs above the CMC, although enhancement activity is seen at concentrations, for the copolymer PLURONIC® L61 (Poly(oxyethylene)-poly(oxypropylene) compounds), as low as 0.0001% wt/vol, or less. The micellar form is also believed to be important to using the copolymers in drug delivery for other reasons, as will be discussed below.

The schematic below is helpful in understanding the relationship between the hydrophobe percentage and the hydrophobe weight of a copolymer and various aspects of the present invention. In the schematic, the weight of the hydrophobe (poly(oxypropylene)) and of the copolymer are shown directly under each identified copolymer. Adjacent to these values are the hydrophobe percentage values for each copolymer.

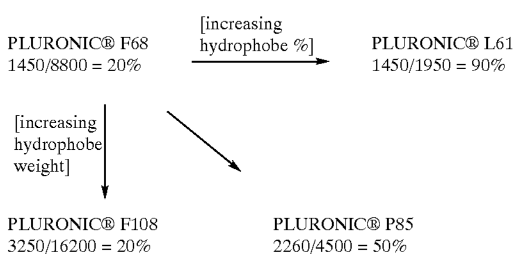

PLURONIC® F68 has been determined to have only a modest activity in enhancing the potency of biological agents. Pluronic L61, which has the same hydrophobe weight as PLURONIC® F68 but a much higher hydrophobe percentage, is generally the most effective of the block copolymers identified in the schematic. PLURONIC® F108, which has the same hydrophobe percentage as PLURONIC® F68 but a much higher hydrophobe weight, is also an effective copolymer, though much less effective than PLURONIC® L61. PLURONIC® P85 has a greater hydrophobe weight and a greater hydrophobe percentage than PLURONIC® F68, but the difference in each value is less than it is for PLURONIC® F108 and L61, respectively. The effectiveness of PLURONIC® P85 in enhancing the potency of biological agents is intermediate between the effectiveness of PLURONIC® F108 and of PLURONIC® L61. These differences in effectiveness are exemplified when various copolymers, at a concentration above CMC, and doxorubicin are incubated in vitro with drug-resistant cells. The ratio of the $IC_{50}$ value for doxorubicin in the absence of copolymer to the ratio in the presence of copolymer is the "resistance reversion index." The resistance reversion index values for various copolymers are:

| Doxorubicin formulation | $IC_{50}$, ng/ml | Resistance reversion index |
|---|---|---|
| free drug | 60,000 | n.a. |
| +5% (w/v) PLURONIC ® F68 | 60,000 | 1 |
| 0.01% (w/v) PLURONIC ® F108 | 10,000 | 6 |
| 0.01% (w/v) PLURONIC ® P85 | 2,000 | 30 |
| 0.01% (w/v) PLURONIC ® L61 | 60 | 1000 |

The importance of the micellar form in delivering biological agents is also revealed in in vivo experiments. In the micellar form, biological agents are located in the hydrophobic core of the micelles, thereby masked by the hydrophilic shell (composed of A-type segments) surrounding the micelles. This masking decreases interactions with liver, plasma proteins, other non-target tissues and other molecules that can bind or inactivate the agent or convert the agent to a toxic metabolite. For example, rapid metabolism of anthracycline antibiotics by the liver leads to the formation of cardiotoxic metabolites that are modified at the C13 position. See, Mushlin et al., Br. *J. Pharmacol.* 110: 975–982, 1993. Using doxorubicin as a model drug, the micellar form decreases liver uptake, decreases conversion to doxorubicinol, and decreases the rate at which the concentration of doxorubicin in the blood decreases.

The effectiveness of copolymers in (a) forming micelles (where greater effectiveness is measured in reduced CMCs) and (b) favoring the partitioning of various biological agents to the micellar rather than the free form of various biological agents increases according to the same pattern. Thus, the hierarchy of effectiveness is again L61>P85>F108>>F68. The presence of micelles at low concentrations is believed to help assure, assuming that biological agent remains associated with the micelles, that the biological agent and the copolymer arrive together at a target tissue. Partitioning coefficients that favor the micellar form help assure that the assumption that the biological agent remains associated with micelles will hold true. The micellar form of the biological agent is also believed to protect the biological agent from uptake by non-target tissues, which tissues may metabolize the biological agent into an ineffective or toxic metabolite, and non-specific adsorption to blood components, cellular components and the like.

At high concentrations, block copolymers can be toxic to the liver, kidney or other cells of a subject. See, BASF Corp., *Pluronic Material Safety Data Sheet and Drug Master Files.* The toxicity of block copolymers increases with the hydrophobicity parameters of block copolymers according to the same pattern seen for increases in effectiveness in potentiating biological agents. Fortunately, the rate of increase in potency as these hydrophobicity parameters change is much greater than the increase in copolymer toxicity. For instance, as illustrated in Example 20, the $LD_{50}$ of L61 in BALB/c mice is 10-fold lower than the $LD_{50}$ of PLURONIC® F108. However, the difference in the optimal therapeutic dose is more than 100 fold improved for PLURONIC® L61 vs. PLURONIC® F108. (See Example 14.) Thus, the concentration range over which effectiveness in potentiating the activity of a biological agent can be maintained while avoiding toxicity due to copolymer is increased for PLURONIC® L61 vs. PLURONIC® F108.

Without wishing to be bound to a particular theory, it is believed that the compositions of the invention reverse efflux mechanisms mediated by members of the glycoprotein P family and other drug resistance mechanisms.

The compositions of the invention are intended to include either preformed micelles with a substantial portion of the biological agent incorporated therein, or copolymer compositions which form micelles with a substantial portion of the agent dissolved therein during the course of the administration of the biological agent to a patient, or subsequent thereto. For the targeting embodiment of the invention, the targeting moiety will either be pre-associated with micelles or will associate with micelles during the course of administration. Particularly preferred block copolymers are those that have low CMC values in isotonic solutions at physiological temperatures. Such block copolymers will maintain a micellar delivery vehicle for biological agents even after substantial dilution into a physiological fluid such as a treatment subject's blood. Such low CMC values allow for the use of reduced levels of block copolymers in the drug composition of the invention.

The invention is described below with reference to the fragmental constants developed by Hansch and Leo. See Hansch and Leo, *Substituent Constants for Correlation Analysis in Chemistry and Biology,* Wiley, New York, 1979; James, *Solubility and Related Properties,* Marcel Dekker, New York, 1986, pp. 320–325. These constants were developed for use in estimating the contribution of a portion of a molecule to the tendency of the molecule to partition between the phases formed by octanol-water mixtures. These constants are generally referred to as Hansch-Leo fragmental partition constants (hereinafter "Hansch-Leo fragmental constants").

The entire disclosure of U.S. application Ser. No. 08/478, 978, entitled "Biological Agent Compositions,", filed concurrently herewith on Jun. 7, 1995 now U.S. Pat. No. 5,817,321 is incorporated herein by reference, as is the entire disclosure of U.S. patent application Ser. No. 08/054,403, filed Apr. 28, 1993.

The number of repeating units of the total hydrophilic (A-type) blocks or the total hydrophobic (B-type) blocks for a polyether copolymer are preferably between about 4 and about 400. More preferably, the number of repeating units is between about 4 and about 200, still more preferably, between about 5 and about 80. The repeating units that comprise the blocks, for A-type and B-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

Preferably, all of the repeating units that comprise A-type blocks have a Hansch-Leo fragmental constant of less than about −0.4, more preferably, less than about −0.5, still more preferably, less than about −0.7. Preferably, all of the repeating units that comprise B-type blocks have a Hansch-Leo fragmental constant of about −0.30 or more, more preferably about −0.20 or more.

Polymers according to the first embodiment of the invention are exemplified by the block copolymers having the formulas:

(V)

or

-continued (VI)

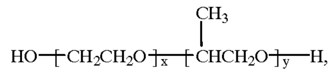

or (VII)

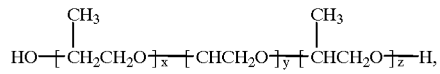

or (VIII)

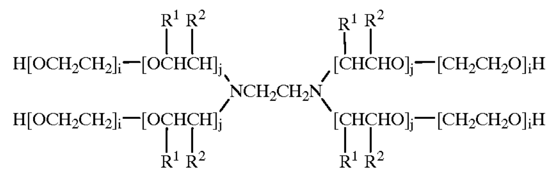

in which x, y, z, i and j have values consistent with the parameters for polyether copolymers described above, and wherein for each $R^1$, $R^2$ pair, one shall be hydrogen and the other shall be a methyl group. Formulas (V) through (VII) are oversimplified in that, in practice, the orientation of the isopropylene radicals within the B block will be random. This random orientation is indicated in formula (VIII), which is more complete. Such poly(oxyethylene)-poly(oxypropylene) compounds have been described by Santon, *Am. Perfumer Cosmet.* 72(4):54–58 (1958); Schmolka, *Loc. cit.* 82(7) :25–30 (1967); *Non-ionic Surfactants,* Schick, ed. (Dekker, NY, 1967), pp. 300–371. A number of such compounds are commercially available under such generic trade names as "poloxamers," "pluronics" and "synperonics." Pluronic polymers within the B-A-B formula are often referred to as "reversed" pluronics, "pluronic R" or "meroxapol." The "polyoxamine" polymer of formula (VIII) is available from BASF (Wyandotte, MI) under the tradename TETRONICM®. The order of the polyoxyethylene and polyoxypropylene blocks represented in formula (VIII) can be reversed, creating TETRONIC R®, also available from BASF. See, Schmolka, *J. Am. Oil Soc.,* 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename PLURADOT®.

A number of pluronics are designed to meet the following formula:

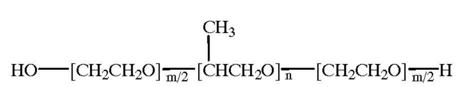

Of course, the ordinarily skilled artisan will recognize that the values of m and n will usually represent a statistical average and that the number of repeating units of the first block of a given molecule will generally not be exactly the number of repeating units of the third block. The characteristics of a number of pluronics, described with reference to formula (IX), are as follows:

| Copolymer | Hydrophobe weight | CMC (% w/v) | Hydrophobe percentage |
|---|---|---|---|
| PLURONIC ® L61 | 1750 | 0.0003 | 90 |
| PLURONIC ® L64 | 1750 | 0.002 | 60 |
| PLURONIC ® F68 | 1750 | 4–5 | 20 |
| PLURONIC ® P85 | 2250 | 0.005–0.007 | 50 |
| PLURONIC ® F127 | 4000 | 0.003–0.005 | 30 |
| PLURONIC ® F108 | 3250 | .0035–0.007 | 20 |

These CMC values were determined by the surface tension method described in Kabanov et al., *Macromolecules* 28: 2303–2314, 1995.

Additional specific poly(oxyethylene)-poly(oxypropylene) block copolymers relevant to the invention include:

| PLURONIC ® | Hydrophobe Weight | Hydrophobe Percentage |
|---|---|---|
| L31 | 950 | 90% |
| F35 | 950 | 50% |
| L42 | 1200 | 80% |
| L43 | 1200 | 70% |
| L44 | 1200 | 60% |
| L62 | 1750 | 80% |
| L63 | 1750 | 70% |
| L64 | 1750 | 60% |
| P65 | 1750 | 50% |
| L72 | 2050 | 80% |
| P75 | 2050 | 50% |
| L81 | 2250 | 90% |
| P84 | 2250 | 60% |
| F87 | 2250 | 30% |
| F88 | 2250 | 20% |
| L92 | 2750 | 80% |
| F98 | 2750 | 20% |
| L101 | 3250 | 90% |
| P103 | 3250 | 70% |
| P104 | 3250 | 60% |
| P105 | 3250 | 50% |
| F108 | 3250 | 20% |
| L121 | 4000 | 90% |
| L122 | 4000 | 80% |
| L123 | 4000 | 70% |
| F127 | 4000 | 30% |
| 10R5* | 1000 | 50% |
| 10R8 | 1000 | 20% |
| 12R3 | 1200 | 70% |
| 17R2 | 1700 | 80% |
| 17R1 | 1700 | 90% |
| 17R2 | 1700 | 80% |
| 17R4 | 1700 | 60% |
| 17R8 | 1700 | 20% |
| 22R4 | 2200 | 60% |
| 25R1 | 2500 | 90% |
| 25R2 | 2500 | 80% |
| 25R4 | 2500 | 60% |
| 25R5 | 2500 | 50% |
| 25R8 | 2500 | 50% |
| 31R1 | 3100 | 90% |
| 31R2 | 3100 | 80% |
| 31R4 | 3100 | 60% |

*All copolymers above this conform to formula (IX), this copolymer and those below conform to formula (VII).

The diamine-linked pluronic of formula (VIII) can also be a member of the family of diamine-linked polyoxyethylene-polyoxypropylene polymers of formula:

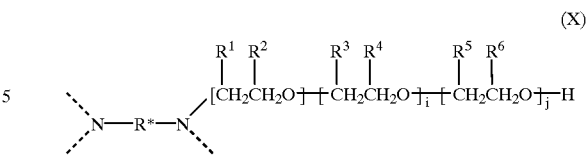

(X)

wherein the dashed lines represent symmetrical copies of the polyether extending off the second nitrogen, $R^*$ an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen. The —$NH_2$—$CH_2CH_2$—$NH_2$— group of of formula (VIII) and the N—$R^*$—N group of formula (X) are examples of linking groups, L, of formula (IV).

Those of ordinary skill in the art will recognize, in light of the discussion herein, that even when the practice of the invention is confined for example, to poly(oxyethylene)-poly(oxypropylene) compounds, the above exemplary formulas are too confining. An important feature is that the average Hansch-Leo fragmental constant of the monomers in an A-type block be about −0.4 or less. Thus, the units making up the first block need not consist solely of ethylene oxide. Similarly, not all of the B-type block need consist solely of propylene oxide units. Instead, the blocks can incorporate monomers other than those defined in formulas (V)–(X), so long as the parameters of the first embodiment are maintained. Thus, in the simplest of examples, at least one of the monomers in block A might be substituted with a side chain group as previously described.

In another aspect, the invention relates to a drug composition made up of a block copolymer at least one of formulas (I)–(X), wherein the A-type and B-type blocks are substantially made up of repeating units of formula —O—$R^5$, where $R^5$ is:

(1) —$(CH_2)_n$—$CH(R^6)$—, wherein n is zero or an integer from about 1 to about 5 and $R^6$ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 to about 6 carbon atoms, alkylcarboxyalkyl, wherein each alkyl independently has about 1 to about 6 carbon atoms, aminoalkyl wherein the alkyl has about 1 to about 6 carbon atoms, alkylamine or dialkylamino, wherein each alkyl independently has about 1 to about 6 carbon atoms, mono- or di-alkylaminoalkyl wherein each alkyl independently has about 1 to about 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;

(2) a carbocyclic group having about 3 to about 8 ring carbon atoms, wherein the group can be for example, cycloalkyl or aromatic groups, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions, or (3) a heterocyclic group, having about 3 to about 8 ring atoms, which can include heterocycloalkyl or heteroaromatic groups, which can include from about 1 to about 4 heteroatoms selected from the group consisting of oxygen, nitrogen, sulfur and mixtures thereto, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions.

Preferably, n is an integer from about 1 to about 3. The carbocyclic or heterocyclic groups comprising $R^5$ preferably have from about 4 to about 7 ring atoms, more preferably about 5 about 6. Heterocycles preferably include from about 1 to about 2 heteroatoms, more preferably, the heterocycles have one heteroatom. Preferably, the heterocycle is a carbohydrate or carbohydrate analog.

Those of ordinary skill will recognize that the monomers required to make these polymers are synthetically available. See, Vaughn et al., *J. Am. Oil Chem. Soc.* 28: 294, 1951. In some cases, polymerization of the monomers will require the use of suitable protective groups, as will be recognized by those of ordinary skill in the art. Generally, the A and B-type blocks are at least about 80% comprised of —$OR^5$— repeating units, more preferably at least about 90%, yet more preferably at least about 95%.

In another aspect, the invention relates to a drug composition made up of a block copolymer of one of formulas (I)–(X) wherein the A-type and B-type blocks consist essentially of repeating units of formula —O—$R^7$—, wherein $R^7$ is a $C_1$ to $C_6$ alkylene group.

The Hansch-Leo estimate of the octanol-water partitioning coefficient (P) for an organic molecule is calculated by the following formula:

$$\text{Log } P = \Sigma a_n f_n + \Sigma b_m F_m$$

where the $f_n$ values are the fragmental constants for the different groups in the molecule, the $a_n$ values are the number of any type of group in the molecule, the $F_m$ values are factors for certain molecular features such as single bonds or double bonds, and the $b_m$ values are the number of any such molecular feature. For instance, the Hansch-Leo fragmental constant for an ethylene oxide repeating unit (—$CH_2CH_2O$—) would be:

$$2f_c + 4f_H + f_o + (4-1)F_b = 2(0.20) + 4(0.23) + (-1.82) + 3(-0.12) = -0.86$$

The Hansch-Leo fragmental constant for a propylene oxide (—$CH_2CH(CH_3)O$—) repeating unit would be:

$$2f_c + f_{CH^3} + 3f_H + f_o + (4-1)F_b = 2(0.2) + 0.89 + 3(0.23) + (-1.82) + 3(-0.12) = -0.2$$

Those of ordinary skill in the art will recognize that the Hansch-Leo approach to estimating partition constants, in which approach the Hansch-Leo fragmental constants are applied, does not yield precisely the empirical partition constant. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. However, the approach is precise enough to define the hydrophobicity features of the polymeric delivery vehicle.

The block copolymers utilized in the invention will preferably form micelles in isotonic aqueous solutions at a physiological temperature having diameter from about 10 nm to about 100 nm. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a CMC that is characteristic of the amphiphile. By varying the sizes of the hydrophilic and hydrophobic segments of the block copolymers, the tendency of the copolymers to form micelles at physiological conditions, as well as the average size of the micelles formed at physiological conditions, can be varied. These tendencies can also be adjusted by blending copolymers with differing mixes of hydrophobic and hydrophilic blocks. The micelles have a dense core formed by the water insoluble repeating units of the B blocks and lipophilic portions of a biological agent dissolved therein, and a hydrophilic shell formed by the A blocks and hydrophobic portions of the biological agent. The micelles have translational and rotational freedom in aqueous environment, and aqueous environments containing the micelles have low viscosity similar to water. Micelle formation typically occurs at copolymer concentrations from about 0.001 to 5% (w/v).

The small size of the micelles formed by block copolymers of the invention is believed to allow these micelles to penetrate in small capillaries and to be taken up by cells. The micelles also can incorporate large amounts of appropriate biological agents. For instance, micelles formed by PLURONIC® L61 can incorporate at least 1 mg of doxorubicin per 2 mg of copolymer.

The effective retention of a drug within the micelles of the invention can be quantified in terms of the partitioning coefficient (P) determined using formula:

$$P = [\text{Agent}]_m / [\text{Agent}]_{aq}$$

where $[\text{Agent}]_{aq}$ is the concentration of biological agent in an aqueous environment outside of the micelles and $[\text{Agent}]_m$ is the concentration of agent in the micelles. In some cases, P is facilely and accurately estimated based on the difference fluorescence properties of certain agents when in an aqueous vs. a more hydrophobic environment.

A minor portion of a targeting molecule made up of a targeting moiety coupled to a lipophilic moiety comprising a hydrocarbon having from about 3 to about 41 carbon atoms is incorporated into the micelles of the compositions of the targeting embodiment of the invention. This portion typically comprises no more than about 10% w/w of the copolymer components of a composition. The lipophilic moieties are believed to act as hydrophobic "anchors", which are incorporated non-covalently into the block-copolymer micelles so that the targeting moiety becomes part of, but extends beyond, the micelle. Such targeting moieties are preferably also incorporated into the micelles used in the brain chemotherapy embodiment of the invention. However, for the brain chemotherapy embodiment the lipophilic moiety can be any lipophilic moiety effective to non-covalently associate the targeting moiety with the micelles. For the brain chemotherapy embodiment, the lipophilic moiety can be, for example a fatty acid residue, a lipid, phospholipid, or a natural or synthetic polymer. Because of availability and ease of use, lipophilic moieties containing hydrocarbon groups such as fatty acid residues are preferred.

The targeting moieties have affinity for a cellular, tissue, viral or substratum site. Typical targeting moieties include without limitation antibodies and hormones with affinity for a cellular binding component, any molecule containing a carbohydrate moiety recognized by a cellular binding component and drugs that bind to a cellular binding component. The phrase "binding component" includes both receptor and acceptor molecules. Preferably, the binding component is a cell-surface binding component. Both polyclonal and monoclonal antibodies which are either available commercially or described in the literature can be employed. Alternatively the ligand can be a naturally occurring protein, such as insulin, that binds to a target site. A non-limiting example of a targeting moiety is the anti-$\alpha_2$GP antibody to brain glial cells ($\alpha_2$-glycoprotein) which is described by Slepnev et al., *Bioconjugate Chem.* 3: 273–274, 1992.

To retain as much of the specificity of the polypeptide, preferably only one or two lipophilic moieties are bound to each polypeptide molecule. This binding can be achieved by the method described by Kabanov et al. *Protein Engineering*, 3, 39–42 (1989), the contents of which are incorporated herein by reference. In this method the lipophilic moiety or a reactive analog thereof is reacted with the targeting moiety in the presence of the surfactant sodium bis-(2-ethylhexyl)sulfosuccinate {AOT®}, octane and a small amount of water will form reversed micelles, that is micelles with water on the inside and octane on the outside. These reversed micelles serve as microreactors allowing uniform point modification of the polypeptide molecules with lipophilic moieties. Reactive derivatives of fatty acids such as stearoyl chloride or lauroyl chloride can be reacted with polypeptides or other hydrophilic targeting moieties using this reaction system. Because the reaction system allows for the level of fatty acyl substitution to be limited, greater biological activity and solubility of the targeting moiety is generally preserved.

For polyethylene oxide-polypropylene oxide copolymer, the hydrophilic/hydrophobic properties, and micelle forming properties of a block copolymer are related to the value of the ratio, n. The ratio, n, is defined as:

$$n = (|B|/|A|) \times (b/a) = (|B|/|A|) \times 1.32$$

where |B| and |A| are the number of repeating units in the hydrophobic and hydrophilic blocks of the copolymer, respectively, and b and a are the molecular weights for the respective repeating units. The value of n will typically be between about 0.2 and about 9.0, more preferably, between about 0.2 and about 1.5. Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. When copolymers other than polyethylene oxide-polypropylene oxide copolymers are used, similar approaches can be developed to relate the hydrophobic/hydrophilic properties of one member of the class of polymers to the properties of another member of the class.

The pharmaceutical compositions of the invention can be administered by a number of routes, including without limitation orally, topically, rectally, vaginally, by pulmonary route, for instance, by use of an aerosol, or parenterally, including but not limited to intramuscularly, subcutaneously, intraperitoneally, intra-arterially or intravenously. The compositions can be administered alone, or can be combined with a pharmaceutically-acceptable carrier or excipient according to standard pharmaceutical practice. For the oral mode of administration, the compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the compositions can be combined with emulsifying and suspending agents. If desired, certain sweetening and/or flavoring agents can be added. For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Suppository forms of the compositions of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycol of various molecular weights and fatty acid esters of polyethylene glycol. See, Remington's Pharmaceutical Sciences, 16th Ed., Mack Publishing, Easton, Pa., 1980, pp. 1530–1533 for further discussion of suppository dosage forms. Analogous gels or creams can be used for vaginal, urethral and rectal administrations.

The chemotherapeutic agents appropriate for use in this invention include, without limitation, vinca alkaloids such as vincristine and vinblastine, mitomycin-type antibiotics such as mitomycin C and N-methyl mitomycin C, bleomycin-type antibiotics such as bleomycin A2, antifolates such as methotrexate, aminopterin, and dideaza-tetrahydrofolic acid, colchicine, demecoline, etoposide, taxanes such as paclitaxel (TAXOL®), anthracycline antibiotics and others. The anthracycline antibiotics exemplify drugs having delivery problems due to low stability, the development of drug resistance in the target tissue, or rapid metabolism. These antibiotics typically include a fused tetracycline aglycone ring system joined at the 7-position to daunosamine. They include, for instance, the compounds represented by the formula:

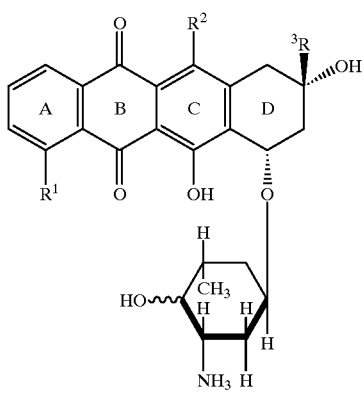

wherein R¹ is hydroxy or methoxy; R² is hydrogen or hydroxy; and R³ is ethyl, acetyl, hydroxyacetyl, or an ester of hydroxyacetyl. These tetracycline antibiotics, like many anti-neoplastic agents, are believed to act by intercalating between the planar aromatic ring structures of DNA, thereby interfering with DNA replication. See, Neidle and Waring, *Molecular Aspects of Anti-Cancer Drug Action*, Pitman Press, 1983. Neoplastic cells are generally particularly susceptible, since they are actively replicating and thus synthesizing replica copies of their DNA. Such tetracycline antibiotics include, without limitation, doxorubicin, daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate, or adriamycin-14-naphthaleneacetate.

Preferred classes of biological agents (including chemotherapeutic agents) include anti-neoplastic agents, antibacterial agents, antiparasitic agents, anti-fungal agents, CNS agents, immunomodulators and cytokines, toxins amd neuropeptides. Biological agents for which target cells tend to develop resistance mechanisms are also preferred. Particularly preferred biological agents include anthracyclines such as doxorubicin, daunorubicin, epirubicin, idarubicin, mithoxanthrone or carminomycin, vinca alkaloids, mitomycin-type antibiotics, bleomycin-type antibiotics, azole antifungals such as fluconazole, polyene antifungals such as amphotericin B, taxane-related antineoplastic agents such as paclitaxel and immunomodulators such as tumor necrosis factor alpha (TNFα), interferons and cytokines.

Preferred biological agents (including chemotherapeutic agents) include without limitation additional antifungal agents such as amphotericin B, flucytosine, ketoconazole, miconazole, itraconazole, griseofulvin, clotrimazole, econazole, terconazole, butoconazole, ciclopirox olamine, haloprogin, tolnaftate, naftifine, nystatin, natamycin, undecylenic acid, benzoic acid, salicylic acid, propionic acid and caprylic acid. Such agents further include without limitation antiviral agents such as zidovudine, acyclovir, ganciclovir, vidarabine, idoxuridine, trifluridine, foxcarnet, amantadine, rimantadine and ribavirin. Such agents further include without limitation antibacterial agents such as penicillin-related compounds including β-lactam antibiotics, broad spectrum penicillins and penicillinase-resistant penicillins (such as methicillin, nafcillin, oxacillin, cloxacillin, dicloxacillin, amoxicillin, ampicillin, ampicillin-sulbactam, azocillin, bacampicillin, carbenicillin, carbenicillin indanyl, cyclacillin, meziocillin, penicillin G, penicillin V, piperacillin, ticarcillin, imipenem and aztreonam), cephalosporins (cephalosporins include first generation cephalosporins such as cephapirin, cefaxolin, cephalexin, cephradine and cefadroxil; second generation cephalosporins such as cefamandole, cefoxitin, cefaclor, cefuroxime, cefuroxime axetil, cefonicid, cefotetan and ceforanide; third generation cephalosporins such as cefotaxime, ceftizoxime, ceftriaxone, cefoperazone and ceftazidime), tetracyclines (such as demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Such agents further include agents active against protozoal infections such as chloroquine, diloxanide furoate, emetine or dehydroemetine, 8-hydroxyquinolines, metronidazole, quinacrine, melarsoprol, nifurtimox, pentamidine, sodium stibogluconate and suramin.

A variety of central nervous system agents are suitable for use in the present composition. These include neuroleptics such as the phenothiazines (such as compazine, thorazine, promazine, chlorpromazine, acepromazine, aminopromazine, perazine, prochlorperazine, trifluoperazine, and thioproperazine), rauwolfia alkaloids (such as reserpine and deserpine), thioxanthenes (such as chlorprothixene and tiotixene), butyrophenones (such as haloperidol, moperone, trifluoperidol, timiperone, and droperidol), diphenylbutylpiperidines (such as pimozide), and benzamides (such as sulpiride and tiapride); tranquilizers such as glycerol derivatives(such as mephenesin and methocarbamol), propanediols (such as meprobamate), diphenylmethane derivatives (such as orphenadrine, benzotrapine, and hydroxyzine), and benzodiazepines(such as chlordiazepoxide and diazpam); hypnotics (such as zolpdem and butoctamide); β-blockers (such as propranolol, acebutonol, metoprolol, and pindolol); antidepressants such as dibenzazepines (such as imipramine), dibenzocycloheptenes (such as amitriptyline), and the tetracyclics (such as mianserine); MAO inhibitors (such as pheneizine, iproniazide, and selegeline); psychostimulants such as phenylethylamine derivatives (such as amphetamines, dexamphetamines, fenproporex, phentermine, amfepramone, and pemline) and dimethylaminoethanols (such as clofenciclan, cyprodenate, aminorex, and mazindol); GABA-mimetics (such as progabide), alkaloids (such as co-dergocrine, dihydroergocristine, and vincamine); cholinergics (such as citicoline and physosigmine); vasodilators (such as pentoxifyline); and cerebro active agents (such as pyritinol and meclofenoxate); as well as mixtures of several such agents.

Of particular interest are sedative-hypnotics such as the benzodiazepines, psychopharmacological agents such as the phenothiazines, thioxanthenes, butyrophenones, and dibenzoxazepines, and central nervous system stimulants. Since, the brain treatment embodiment of the invention is directed to compositions that improve the activity of biological agents, this embodiment of the invention can be applied to a wide variety of central nervous system agents by applying the principles and procedures described herein.

The dosage for a biological agent in a micellar composition will often be about that of the biological agent alone;

dosages will be set by the prescribing medical professional considering many factors including the age, weight and condition of the patient and the pharmacokinetics of the agent. Often the amount of a micellar form of an agent required for effective treatment may be less than the amount required using the free biological agent. For daunorubicin use in treating cancer, a typical dosage will be about 1 mg per kg of body weight. Vinblastine is typically administered at a dose of from 0.1 to 0.2 mg per kg of body weight.

Generally, the biological agents used in the invention are administered to an animal in an effective amount. The effect of the copolymer used in the composition on effectiveness must be considered in determining effective amount. Generally, an effective amount is an amount effective to either (1) reduce the symptoms of the disease sought to be treated or (2) induce a pharmacological change relevant to treating the disease sought to be treated. For cancer, an effective amount includes an amount effective to: reduce the size of a tumor; slow the growth of a tumor; prevent or inhibit metastases; or increase the life expectancy of the affected animal. The present invention provides for a method of treating cancers wherein the cancer is a leukemia, breast cancer, ovarian cancer, pancreatic cancer, lung cancer, myeloma, melanoma, glioma or astrocytoma. The present invention also provides the method of treating cancer, wherein the cancer is Hodgkin's lymphoma, non-Hodgkin's lymphoma, acute lymphocytic lymphoma, acute myelocytic lymphoma, acute non-lymphatic leukemia, Karposi's sarcoma, small-cell lung cancer, non-small-cell lung cancer or glial astrocytoma.

In many cases, the metabolites of various biological agents create or enhance the unwanted effects resulting from administering the agent. This is certainly the case for anthracycline-based drugs, where metabolites are believed to lead to cardiotoxicity. See, Mushlin et al., Br. *J. Pharmacol* 110: 975–982, 1993. The copolymer compositions of the invention can decrease the rate of metabolism for biological agents, thereby reducing the potential for harmful side effects.

Penetration of the brain by a biological agent can be measured by a number of techniques, as will be recognized by those of ordinary skill in the art. Such methods include isotope labeling, assessing animal behavior for the effects of a biological agent, and measuring lethal dosages for drugs with toxic effects that occur at the brain. Such methods further include measuring decreases in the dosage required to elicit the appropriate biological response.

Various antifungal agents successfully treat human fungal infections. However, the therapeutic dose is often a compromise between achieving effectiv drug levels and avoiding toxic side effects. In recent years, the emergence of drug resistance among intrinsically sensitive species such as *Candida albicans* and the increasing incidence of intrinsically drug resistant species such as *Candida kruset* has prompted a search for newer antifungal agents.

Although fluconazole has a low incidence of side effects, the incidence of resistance is an increasing problem. Delievery vehicles that are effective in enhancing chemotherapeutic activity and reversing resistance to such agents is therefore desireable for this agent, as well as for other antimicrobial agents.

The invention is exemplified by the following non-limiting examples.

EXAMPLE 1

Micelle Size

Block copolymers of poly(oxyethylene)-poly (oxypropylene) having the ratios of poly(oxypropylene) to poly(oxyethylene) indicated below were dispersed in RPMI 1640 medium at the concentrations indicated below. The mixtures were incubated for 40 minutes at 30° C. The average micelle diameter was measured by quasielastic light scattering. See Kabanov et al., *Macromolecules* 28: 2303–2314, 1995. The results were as follows:

| copolymer | conc. (% w/v) | Avg. Diameter |
| --- | --- | --- |
| F-68 | 1.0% | 726.0 nm |
| P-85 | 1.0% | 18.0 nm |
| L-64 | 1.0% | 20.4 nm |
| 1:1.5 P-85:L-64 | 0.01% | 17.0 nm |
| 1:2.5 F-68:L-64 | 1.0% | 33.5 nm |

EXAMPLE 2

Fatty acyl conjugates

A solution of 50 μl of 2 mg/ml of anti-$\alpha_2$GP antibody specific for the $\alpha_2$-glycoprotein of glial cells (Chekhomim et al., *FEBS Lett.* 287: 149–152, 1991) in 0.1 M borate buffer (pH 8.5) was mixed into 2 ml of 0.1 M AOT® {sodium bis(2-ethylhexyl)sulfosuccinate, available from Serva Chemicals, Germany} in octane. A reaction is initiated by adding a two-fold molar excess (with respect to the polypeptide) of stearic acid chloride in 0.2 ml of 0.1 M AOT® in octane to the mixture. The stearic acid chloride was obtained from staric acid (available from Reakhim, Russia) as described in Kabanov et al., *Molek Biologiya* (Russian), 22: 473–484 (Engl. edn.: 382–391), 1988. The reaction was conducted overnight at 25° C. The product is precipitated three times with cold acetone, dissolved in RPMI 1640 medium and sterilely filtered through a 0.22 μm filter. (The polyclonal antibody used in this experiment also reacted with glial fibrillary acidic protein.)

EXAMPLE 3

Iodinated targeting moieties

Anti-$\alpha_2$GP antibody was labelled with $^{125}$I using Bolton-Hunter reagent in the system of reversed micelles of AOT® in octane as described in Slepnev V. I. et al., *Bioconjugate Chem.*, 3, 273–274 (1992). Specific radioactivity of the $^{125}$I-labelled protein ranges from 19 to 21 Ci/mol.

Wistar rats (80 g body weight, 8 animals/group) were injected i.p. (0.1 ml/10 g body weight) with a composition made up of the $^{125}$I-labelled anti-$\alpha_2$GP antibody (1 mCi/ml) dissolved in a mixture of 1.5% (w/v) copolymer Pluronic P85 and 2.5% (w/v) copolymer Pluronic L64 dissolved in RPMI 1640 medium. $^{125}$I-labelled polypeptide dissolved in RPMI 1640 medium was administered at the same concentration. After three days the animals were killed, and tissue samples taken for radioactivity assay to analyze tissue distribution as described by Chekhonin et al., *FEBS Lett.*, 287 149–152 (1991). The distribution of radioactivity was quantitated by liquid scintillation counting. The experiments were repeated at least twice and the results were reproducible with less than 10% variation. The results, expressed as the ratio of brain radioactivity to the radioactivity in a given tissue (±S.D.), were as follows:

| Organ | Relative Content of Label | |
|---|---|---|
| | Micelle | Control |
| Brain/heart | 1.22 ± 0.91 | 0.11 ± 0.02 |
| Brain/kidney | 7.42 ± 0.56 | 0.05 ± 0.01 |
| Brain/liver | 9.02 ± 0.75 | 0.01 ± 0.00 |
| Brain/lung | 12.1 ± 0.92 | 0.04 ± 0.01 |
| Brain/spleen | 6.48 ± 0.39 | 0.01 ± 0.00 |
| Brain/blood | 8.85 ± 0.67 | 0.01 ± 0.00 |

EXAMPLE 4
Quantitation of behavioral changes

Quantitative evaluation of changes in behavior reactions {See *Theory in Psychopharmacology*, S. J. Cooper, Ed., Vol. 1, (Academic Press, London, New York, 1981)} are performed. Groups (10 animals/dose point) of DBA/2 male mice (from Kriukovo Veterinary Department of Russian Academy of Sciences, Russia, 20–25 g body weight) with similar characteristics of moving activity are injected i.p. with the test preparations at doses corresponding to 0.10 $LD_{95}$. Concentrations are adjusted so that a maximum volume of 0.1 ml is injected in each mouse. Mouse mobility (the number of mouse migrations in a cell) and grooming characteristics are registered for each group at 30 minute intervals over 15 hours using a Rhema Labortechnik device. The experiments are repeated three times.

EXAMPLE 5
Measuring toxicity

The lethal effect accompanied by development of specific neurologic symptoms described in *Theory in Psychopharmacology*, S. J. Cooper, Ed., Vol. 1, (Academic Press, London, New York, 1981) is measured. Groups (10 animals/dose point) of DBA/2 mice (18–19 g body weight) are injected i.p. with the test preparations. Concentrations are adjusted so that a maximum volume of 0.5 mL is administered to each mouse. For quantitative evaluation of specific lethal action, the lethal dose ($LD_{95}$) is calculated using the probit method on the basis of 10 concentration points. The experiments are repeated at least twice and results should reproducible with less than 10% variation.

EXAMPLE 6A
Micelle formation

A 1:1.5 mixture of PLURONIC® P85 and PLURONIC® L64 having individual ratios (n) of (oxypropylene) to (oxyethylene) blocks of 1.00 and 1.50, respectively, and a combined value (N) of 1.30, was diluted with RPMI 1640 medium to a final concentration of 4.0% at 4° C. The mixture was incubated for 30 minutes at 370C and then sterilized by filtration through a 0.22 μm filter. An equal volume of a solution of 200 μg daunorubicin in RPMI 1640 medium was added and this mixture was incubated for 30 minutes at 37° C.

EXAMPLE 6B
Preparation of brain targeted micelles

Equal volumes of the solution of PLURONIC® micelles of Example 6A and the solution of stearylated antibody of Example 2 were mixed at 37° C. Equal volumes of the resulting solution and a sterile 6 mg/ml solution of haloperidol dissolved in RPMI 1640 were mixed at 37° C.

EXAMPLE 7
Behavioral measure of brain biodistribution

The preparations described in Example 6, except that the anti-GFAP antibody was not radioactive and was used at a concentration of 0.4 mg/ml, were used in these experiments.

Solutions were administered i.p. Animal mortality was monitored daily for 14 days. The $LD_{50}$ and maximum tolerated dosage ("MTD", i.e., the maximal dose at which no animals among 6 equivalently treated animals died) were calculated by probit analysis. See, Chan and Hayes in *Principles and Methods of Toxicology*, Hayes, A. W., ed., Raven Press, New York, 1989, pp. 169–189. When administered in the PLURONIC® vehicle, the $LD_{95}$ value of haloperidol was determined to be 0.15 mg/kg, without the PLURONIC® vehicle, the $LD_{95}$ value of haloperidol was 75 mg/kg.

An amount equaling 10% of the $LD_{.5}$ for a given composition was injected i.p. into DBA/2 mice in 0.5 ml of the PLURONIC® vehicle (Example 6). The behavioral results of these injections (±S.D.), measured as described in Kabanov et al., *J. Controlled Release*, 22:141 (1992), were as follows:

| Behavior | Micellar form of haloperidol | Free haloperidol |
|---|---|---|
| Horizontal mobility | 14.4 ± 64% | 204.6 ± 24% |
| Grooming | 26.5 ± 76% | 1834.8 ± 12.5% |

As can be seen from the above table, the micellar form of haloperidol is markedly more active than an amount of free haloperidol normalized at 10% of the $LD_{95}$ amount.

EXAMPLE 8
Specific and non-specific targeting molecules

A specific targeting compostion was prepared as described in Example 6. The final concentration of the anti-GFAP antibody was 0.02 mg/ml, and its specific radioactivity was 20 Ci/mol.

A non-specific was prepared using the same procedure but substituting a Fab preparation of non-specific murine IgG for the brain-specific antibody. The final concentration of the antibody was 0.02 mg/ml, and its specific radioactivity was 20 Ci/mol.

These preparations (0.5 ml) were injected i.p. into DBA/2 mice. The resulting biodistributions (±S.D.) were:

| Organ | Relative Content of label (% Dose/g of tissue) | |
|---|---|---|
| | Micelle | Control |
| Brain | 53 ± 4.15* | 1.4 ± 0.12 |
| Heart | 3.2 ± 0.22 | 3.1 ± 0.21 |
| Kidney | 4.4 ± 0.31 | 5.1 ± 0.47 |
| Liver | 4.3 ± 0.26 | 36.2 ± 1.92 |
| Lung | 2.2 ± 0.11 | 4.8 ± 0.42 |
| Spleen | 4.1 ± 0.33 | 5.1 ± 0.41 |
| Blood | 3.8 ± 0.31 | 8.7 ± 0.67 |

EXAMPLE 9
Targeting using neuronal-specific anti-enolase antibody

A targeting composition was made using the procedure of Example 6 wherein the antibody was a monoclonal antibody against the γ-subunit of neuronal-specific enolase ("anti-NSE MAb", available from Russian Research Center, Moscow, Russia). The final concentration of the antibody was 0.35 mg/ml, and its specific radioactivity was 18 Ci/mol. For control experiments, the nonspecific murine antibody preparation described in Example 8 was used.

These preparations (0.5 ml) were injected i.p. into DBA/2 mice. The resulting biodistributions (±S.D.) were:

| Organ | Relative Content of label (% Dose/g of tissue) | |
|---|---|---|
| | Micelle | Control |
| Brain | 58 ± 5.12* | 0.9 ± 0.06 |
| Heart | 3.2 ± 0.23 | 2.8 ± 0.21 |
| Kidney | 4.3 ± 0.36 | 5.6 ± 0.52 |
| Liver | 3.8 ± 0.32 | 31.2 ± 3.05 |
| Lung | 2.1 ± 0.18 | 6.4 ± 0.59 |
| Spleen | 3.9 ± 0.33 | 4.9 ± 0.37 |
| Blood | 4.1 ± 0.40 | 7.4 ± 0.71 |

EXAMPLE 10
Targeting using insulin

An insulin targeting molecule was prepared by linking stearyl moieties to insulin (available from Sigma, St. Louis, Mo.) using the method of Example 6. The targeting molecule was incorporated into a haloperidol composition using the method described in Example 6. The final concentration of insulin in the composition was 0.4 mg/ml. The $LD_{95}$ for this haloperidol composition was determined to be 3.0 mg/kg, using the method in Example 7.

An amount equaling 10% of the $LD_{95}$ for a given composition was injected i.p. into DBA/2 mice in 0.5 ml (6 mice per each treatment). The behavioral results of these injections (±S.D.), measured as described in Kabanov et al., *J. Controlled Release*, 22:141 (1992), were as follows:

| Behavior | Micellar form of haloperidol | Free haloperidol |
|---|---|---|
| Horizontal mobility | 56.1 ± 36% | 180.1 ± 26% |
| Grooming | 386.6 ± 29% | 1656.4 ± 6.5% |

As can be seen from the above table, the micellar form of haloperidol is markedly more active than an amount of free haloperidol normalized at 10% of the $LD_{95}$ amount.

EXAMPLE 11
Sulpiride compositions

Sulpiride and the stearylated anti-NSE Fab antibody preparation of Example 9 were incorporated into the block-copolymer micelles using the methods described in Example 6. The final concentration of anti-NSE Fab in the preparation was 2.1 mg/ml. A sterile, control solution of sulpiride in RPMI 1640 medium was prepared The $LD_{95}$ values for the preparations were determined as described in Example 7. For the block copolymer preparation, the $LD_{95}$ was 12.1 mg/kg body weight; for the control preparation it was 100 mg/kg body weight.

EXAMPLE 12
Trifluorperazine compositions

Trifluorperazine and anti-GFAP Fab antibody preparation treated with stearoyl chloride were incorporated into the block-copolymer micelles using the methods described in Example 6. The final concentration of antibody in the preparation was 0.2 mg/ml. A sterile, control solution of trifluorperasin in RPMI 1640 medium was prepared The $LD_{95}$ values for the preparations was determined as described in Example 7. For the block copolymer preparation, the $LD_{95}$ was 0.04 mg/kg body weight; for the control preparation it was 10 mg/kg body weight.

The minimum neuroleptic dose (MND) was determined for each preparation. The minimum neuroleptic dose is defined as the minimum dose that caused a neuroleptic effect as monitored behaviorly. See, Kabanov et al., *FEBS Lett.* 258: 343–345, 1989. The MND for the copolymer-containing preparation was 0.02 mg/kg, while that of the control preparation was 2 mg/kg. The ratio of $LD_{95}$/MND was 50 for the copolymer preparation and 5 for the control preparation.

EXAMPLE 13A
Cytotoxicity against resistant cancer cells

Pluronic P85 was dissolved in RPMI 1640 medium (ICN Biomedicals Inc., Costa Mesa, Calif.) to a final concentration of 1%, and then the solution was sterilized by filtration to remove bacterial or fungal contamination. This Pluronic P85 solution was used to make appropriate dilutions of sterile drug solutions for the cell culture experiments described below.

The cytotoxicity studies utilized the SKOV3 line of transformed cells (hereinafter "SK cells") and the SKVLB cell line derived therefrom (hereinafter "SK-resistant cells"). Both of these cell lines were provided by Dr. V. Ling, University of Toronto. The SK-resistant cell line is a multi-drug resistant cell line derived from the SK cell line by long term cultivation in the presence of vinblastine.

Various dilutions of a number of anticancer agents were made in RPMI medium or the PLURONIC® P85 solution described above. Cells were prepared for use in these experiments by plating an equal volume of a cell suspension (2000–3000 cells) into the wells of 96-well microtiter plates (Costar, Cambridge, Mass.) and cultured for 2 days. All cell culturing was done at 370C and under a 5% $CO_2$ atmosphere. After this, 100 µl per plate of fresh medium (RPMI 1630 medium supplemented with 10% fetal calf serum) was added. The free anticancer agent or copolymer plus anticancer agent dilutions were applied to the wells in 100 µl volumes. The cells were exposed to the free or micellar form of a drug for two hours. After this incubation, the cells were washed three times with fresh medium. Then, the cells were cultured under fresh medium for an additional four days.

The number of viable cells for each culture was determined by standard XTT analysis, which measures the activity of mitochondrial enzymes. See, Scudiero et al., *Cancer Res.*, 48:4827 (1988). 50 µl per well of sterile 1 mg/ml XTT (2,3-bis[2Methoxy-4-nitro-5-sulfophenyl]-2H-tetrazolium-5-carboxanilide inner salt, Sigma, St. Louis, Mo.) in PRMI-1640 containing 5 µl/ml of 1.54 mg/ml phenazine metasulphate (Sigma) in PBS was added to the cells. The cells were incubated for 16 hours, after which the absorbance of each well at 450 nm was determined. The SEM for any value determined (the mean of three determinations) was always with 10% of the value. $IC_{50}$ values (i.e., the concentration at which 50% inhibition was achieved) were determined by extrapolating from graphs plotting the number of viable cells (i.e., the mitochondrial enzyme activity) versus the concentration of drug applied to the cells. The results for SK-resistant cells were as follows:

| Form of biological agent | IC$_{50}$, (ng/ml) |
| --- | --- |
| Free doxorubicin | 60,000 |
| PLURONIC ® L61 | 70 |
| PLURONIC ® P85 | 1000 |
| PLURONIC ® F108 | 2000 |
| PLURONIC ® F68 | 60,000 |

EXAMPLE 14
Copolymer titrations

Figure 1B:
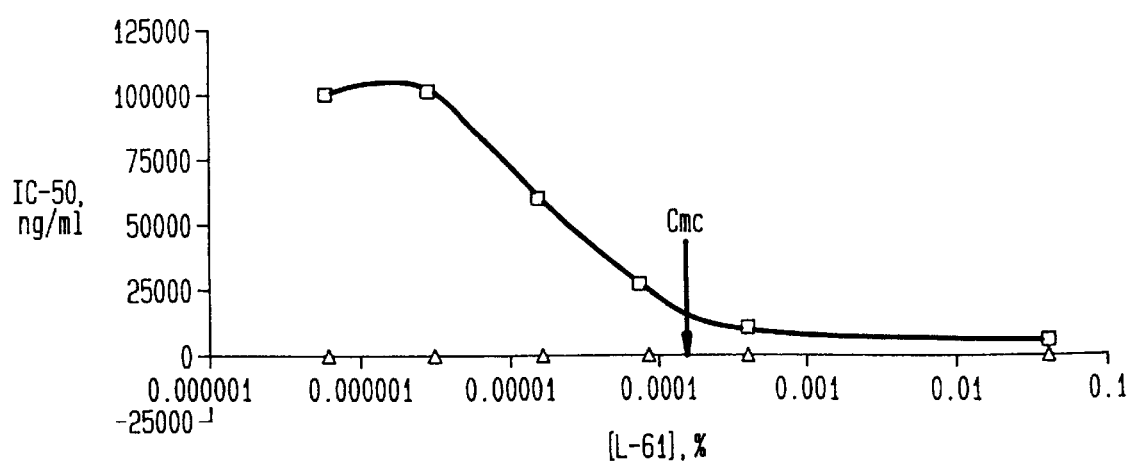

The methodology of Example 13A was used except in two details. The first difference was that doxorubicin-resistant MCF7 cells (MCF ADR® cells, which described further in Example 21) were used in place of SK cells. Second, in addition to varying doxorubicin concentrations, the concentration of copolymer was also varied. The percent inhibition with change in doxorubicin concentration is shown in FIG. 1A for cultures maintained in the presence of varying concentrations of PLURONIC® L61. Line 1 is for free doxorubicin; line 2 is for doxorubicin in the presence of $0.61 \times 10^{-6}$M PLURONIC® L61; line 3 is for doxorubicin in the presence of $0.3 \times 10^{-5}$M PLURONIC® L61; line 4 is for doxorubicin in the presence of $0.16 \times 10^{-4}$M PLURONIC® L61; line 5 is for doxorubicin in the presence of $0.8 \times 10^{-4}$M PLURONIC® L61; line 6 is for doxorubicin in the presence of $0.4 \times 10^{-3}$M PLURONIC® L61; and line 7 is for doxorubicin in the presence of $0.4 \times 10^{-1}$ M PLURONIC® L61. In FIG. 1B, these data are consolidated such that the figure shows the UC$_{50}$ value for doxorubicin applied to the cells in the presence of the indicated concentration of PLURONIC® L61.

EXAMPLE 15
Parenteral composition

A composition suitable for parenteral administration was prepared by dissolving 400 mg of PLURONIC® P-85 and 600 mg of PLURONIC® L-64 in 50 mL of RPMI 1640 at 4° C. The mixture was incubated for 30 minutes at 37° C. and then sterilized by filtration through a 0.22 μm filter. The filtered solution was mixed with a solution of 100 mg of sterile lyophilized haloperidol powder dissolved in 50 mL of RPMI and incubated for 30 minutes at 37° C.

The composition can be stored in the dark at room temperature for 7 days without loss of activity or can be lyophilized and stored for at least 1 year in the dark at room temperature.

EXAMPLE 16
Parenteral composition

A further composition suitable for parenteral administration prepared by dissolving 100 mg of sodium ascorbate in 100 ml of a 9% aqueous solution of sodium chloride. To one-half of this solution were added at 4° C. 400 mg of Pluronic P-85 and 600 mg of Pluronic L-64. The mixture was incubated for 30 minutes at 37° C. and then sterilized by filtration through a 0.22 μm filter.

Separately 100 mg of sterile lyophilized haloperidol powder and 50 mg of glucose were dissolved in the remaining sodium ascorbate-sodium chloride solution and the two solutions were mixed and incubated for 30 minutes at 37° C.

This composition can be stored for 30 days in the dark at room temperature without loss of activity or can be lyophilized and stored for at least 1 year in the dark at room temperature.

EXAMPLE 17
Parenteral composition

A further composition suitable for parental administration prepared by dissolving 100 mg of sodium ascorbate in 100 ml of a 9% aqueous solution of sodium chloride. To one-half of this solution were added at 4° C. 400 mg of Pluronic P-85 and 600 mg of Pluronic L-64. The mixture was incubated for 30 minutes at 37° C. Separately 100 mg of lyophilized haloperidol powder and 50 mg of glucose were dissolved in the remaining sodium ascorbate-sodium chloride solution and the two solutions were mixed and incubated for 30 minutes at 37° C. The combined mixture was sterilized by filtration through a 0.22 μm filter.

This composition can be stored for 30 days in the dark at room temperature without loss of activity or can be lyophilized and stored for at least 1 year in the dark at room temperature.

EXAMPLE 18
Parenteral composition

A parenterally administrable composition was prepared by dissolving 400 mg of PLURONIC® P-85 and 600 mg of PLURONIC® L-64 in 50 ml of aqueous solution containing 1 mg/ml sodium ascorbate and 0.9 g/ml sodium chloride.

The mixture was incubated for 30 min at 37° C. To this was added 100 mg of lyophilized haloperidol powder and 50 mg of glucose dissolved in 50 ml of aqueous solution containing 1 mg/ml sodium ascorbate and 0.9 g/ml sodium chloride and this combined mixture was incubated for 30 min at 37° C. To 100 ml of this preparation were dissolved 40 mg of lyophilized hydrophobized anti-GFAP Fab powder and this solution was incubated for 30 minutes at 37° C. and then sterilized by filtration through a 0.22 μm filter. The composition can be stored in the dark at room temperature for 30 days without any essential loss of activity or can be lyophilized and stored for at least one year in the dark at room temperature.

EXAMPLE 19

A further composition suitable for parenteral administration is prepared by dissolving 100 mg of sodium ascorbate in 100 ml of a 9% aqueous solution of sodium chloride. To this solution are added at 4° C. 10 mg of PLURONIC® L-61. The mixture is incubated for 30 minutes at 37° C. and then sterilized by filtration through a 0.22 μm filter. This solution is packaged together with a container of 10 mg doxorubicin.

EXAMPLE 20
Acute toxicity

The acute toxicity of PLURONIC® F108, P85 and L61 were studies in 5-week old BALB/c male mice. Each experimental group of mice included 6 mice. Various doses of isotonic PLURONIC® solutions were administered i.p. Animal mortality was monitored daily for 14 days. The LD$_{50}$ and maximum tolerated dosage ("MTD", i.e., the dose at which no animals among 6 equivalently treated animals died) were calculated by probit analysis. See, Chan and Hayes in *Principles and Methods of Toxicology*, Hayes, A. W., ed., Raven Press, New York, 1989, pp. 169–189. The results were as follows:

| Pluronic | MTD, g/kg | LD$_{50}$, g/kg |
|---|---|---|
| PLURONIC ® L61 | 0.1 | 0.8 |
| PLURONIC ® P85 | 0.2 | 0.8 |
| PLURONIC ® F108 | 5.0 | 9.0 |

EXAMPLE 21

Treatment of experimental glioma tumor.

The antibodies (Ab) to GFAP and α2-glycoprotein were modified with stearic acid residues as described in example 1. They were also covalently linked to PLURONIC® P85 as described by Kabanov et al. J. Controlled Release, 22:141 (1992).

The therapeutic efficacy of doxorubicin in treatment of glioma was explored. C6 glioma cells were inoculated intracerebrally in groups (n=25) of male Sprague-Dawley rats (280–300 g) obtained from Kriukovo Department of Nursery of Russian Academy of Sciences. 10, 15, 20, and 25 days after inoculation, (a) 10 mg/kg of free doxorubicin, (b) doxorubicin in 1% PLURONIC® P85, (c) doxorubicin in 10% PLURONIC® P85 containing 0.1 mg/ml of Ab modified with stearic acid chloride and (d) doxorubicin in 10% PLURONIC® P85 containing 0.1 mg/ml of Ab linked to PLURONIC® P85 were administered i.p. (volume 1 ml/300 g body weight). Controls will be given injections i.p. with an equal volume of saline. Clinical observations were performed daily. Animals were weighted weekly in the first 2 months and monthly thereafter. Vital signs will be verified to ensure that the animal was dead and necropsy was initiated within 5 min. after the animal died. Data on survival was analyzed to grade the drug effect on tumor incidence and latency. The data were presented as a ratio of median survival times in the treated group (T) and control (C). For necropsy all major organs were saved and fixed in their entirety. The tail (used in the study for animal identification during in-life phase) was saved in formalin with the animal tissues. All brains were removed and trimmed at three different positions. Three sections of the spinal cord were collected at the cervical, thoracic and lumbar level. Trimmed specimen was placed in Tissue Tek cassettes and processed in a tissue processor. Tissue sections were cut at a thickness of 4–6 mm using a microtome and stained with haematoxylin-eosine. Histopathological examinations of brains assessed: (i) the total number of tumors in animals; (ii) the number of tumor bearing animals; and (iii) the histopathological classification and grading of tumors. The results of the experiment are as follows:

| Animal group | Median survival, days | Trial/control × 100% |
|---|---|---|
| Control | 11.2 | — |
| Free doxorubicin | 10.5 | — |
| Micellar doxorubicin | 25.3 | 226 |
| Micellar doxorubicin + stearoylated antibodies | 41.0 | 366 |
| Micellar doxorubicin + conjugated antibodies | 24.5 | 218 |

The histopathological examinations also revealed that 1) free doxorubicin caused no effect on tumor size and number compared to control; 2) all 3 micellar formulations caused significant decrease in tumor size and number; 3) the most pronounced effect was observed in the case of micellar doxorubicin+stearoylated antibodies, in this case tumors were practically not observed.

What is claimed is:

1. A composition comprising:
   (a) a biological agent;
   (b) a polyether block copolymer comprising an A-type linear polymeric segment joined at one end to a B-type linear polymeric segment; and
   (c) a targeting molecule comprising a targeting moiety and a lipophilic moiety, wherein the lipophilic moiety comprises a hydrocarbon having from about 3 to about 41 carbon atoms; and
   wherein said composition forms a micelle.

2. The composition of claim 1, wherein the lipophilic moiety comprises a hydrocarbon having from about 5 to about 25 carbon atoms.

3. The composition of claim 2, wherein the lipophilic moiety comprises a hydrocarbon having from about 9 to about 17 carbon atoms.

4. The composition of claim 1, wherein said polyether block copolymer is selected from the group of polyether block copolymers consisting of $$A\text{-}B\text{-}A', \quad (I)$$

$$A\text{-}B, \quad (II)$$

$$B\text{-}A\text{-}B', \quad (III)$$

or $$L(R^1)(R^2)(R^3)(R^4) \quad (IV)$$

wherein A and A' are A-type linear polymeric segments, wherein B and B' are B-type linear polymeric segments, and wherein $R^1$, $R^2$, $R^3$ and $R^4$ are (1) polyether block copolymers of formulas (I), (II) or (III) or (2) hydrogen and L is a linking group, with the proviso that no more than two of $R^1$, $R^2$, $R^3$ or $R^4$ can be hydrogen, and mixtures thereof.

5. The composition of claim 1, wherein at least 90% of the linkages joining the repeating units for each A-type polymeric segment and B-type polymeric segment comprise ether linkages.

6. The composition of claim 5, wherein the repeating units for each A-type polymeric segment and B-type polymeric segment have molecular weight between 30 and 100.

7. The composition of claim 1 wherein each A-type polymeric segment and B-type polymeric segment consists essentially of repeating units of formula —O—$R^5$, wherein $R^5$ is (1) —(CH$_2$)$_n$—CH(R$^6$)—, wherein n is zero or an integer from about 1 to about 5 and $R^6$ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 to about 6 carbon atoms, alkylcarboxyalkyl, wherein each alkyl group independently has about 1 to about 6 carbon atoms, aminoalkyl wherein the alkyl has about 1 to 6 carbon atoms, alkylamine or dialkylamino, wherein each alkyl independently has about 1 to 6 carbon atoms, mono- or di-alkylaminoaklyl wherein each alkyl independently has about 1 to 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;

(2) a carbocyclic group of up to 8 ring carbon atoms, which is unsubstituted or substituted with alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions, or (3) a heterocyclic group of up to 8 ring atoms and having from 1 to 4 heteroatoms independently selected from the group consisting of oxygen, nitrogen, and sulfur, and which is unsubstituted or substituted with alkyl having about 1 to about 6 carbon atoms, alkoxy having about 1 to about 6 carbon atoms, dialkylamino wherein each alkyl independently has about 1 to about 6 carbon atoms, amino, sulfonyl, hydroxy, carboxyl, fluoro, or chloro substitutions.

8. The composition of claim 1, wherein the hydrophobe weight percentage of the polyether block copolymer is at least 50%.

9. The composition of claim 8, wherein the hydrophobe weight percentage of the polyether block copolymer is at least 60%.

10. The composition of claim 1, wherein wherein the hydrophobe molecular weight of the polyether block copolymer is at least 900.

11. The composition of claim 10, wherein wherein the hydrophobe molecular weight of the polyether block copolymer is at least 1700.

12. The composition of claim 1, wherein the hydrophobe molecular weight of the polyether block copolymer is at least 2000 and the hydrophobe weight percentage of the polyether block copolymer is at least 20%.

13. The composition of claim 1, wherein the composition comprises one or more said polyether block copolymers and the polyether block copolymers have a critical micellar concentration ("CMC") of about 0.5% wt/vol or less at 37° C. in an isotonic aqueous solution.

14. The composition of claim 13, wherein the polyether block copolymers have a CMC of about 0.05% wt/vol or less at 37° C. in an isotonic aqueous solution.

15. The composition of claim 14, wherein the polyether block copolymers have a CMC of about 0.01% wt/vol or less at 37° C. in an isotonic aqueous solution.

16. The composition of claim 1, wherein the polyether block copolymer conforms to the following formula:

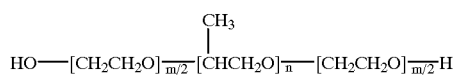

wherein m and n are integers between about 4 and about 400.

17. The composition of claim 16, wherein the hydrophobe weight percentage of the polyether block copolymer is at least 50%.

18. The composition of claim 17, wherein the hydrophobe weight percentage of the polyether block copolymer is at least 60%.

19. The composition of claim 16, wherein the hydrophobe molecular weight of the polyether block copolymer is at least 900.

20. The composition of claim 19, wherein the hydrophobe molecular weight of the polyether block copolymer is at least 1700.

21. The composition of claim 20, wherein the hydrophobe molecular weight of the polyether block copolymer is at least 2000 and the hydrophobe weight percentage is at least 20%.

22. The composition of claim 16, wherein the composition comprises one or more said polyether block copolymers and the polyether block copolymers have a critical micellar concentration ("CMC") of about 0.5% wt/vol or less at 37° C. in an isotonic aqueous solution.

23. The composition of claim 22, wherein the polyether block copolymers have a CMC of about 0.05% wt/vol or less at 37° C. in an isotonic aqueous solution.

24. The composition of claim 23, wherein the polyether block copolymers have a CMC of about 0.01% wt/vol or less at 37° C. in an isotonic aqueous solution.

25. The composition of claim 1, wherein the biological agent is selected from the group consisting of phenothiazines, rauwolfia alkaloids, thiozanthenes, diphenylbutylpiperidines, benzamides, glycerol derivatives, propanediols, dipheylmethane derivatives, benzodiazepines, hypnotics, β-blockers, dibenzazepines, dibenzocycloheptenes, tetracyclics, MAO inhibitors, pheylethylamine derivatives, dimetylaminoethanols, GABA-mimetics, alkaloids, cholinergics, vasodilators, cerebro active agents, chemotherapeutic agents and mixtures thereof.

26. The composition of claim 25, wherein the biological agent is an anti-tumor chemotherapeutic agent.

27. A method of targeting a biological agent to a pre-selected tissue, wherein the method comprises administering to an animal the composition of claim 1.

28. A method of treating cancer comprising administering to an animal a composition comprising;
    (a) a cancer-treating effective amount of a chemotherapeutic agent; and
    (b) a polyether block copolymer comprising an A-type linear polymeric segment having molecular weight contributions between about 30 and about 500, joined at one end to a B-type linear polymeric segment having molecular weight contributions between about 30 and about 500; and
    (c) a targeting molecule comprising a targeting moiety and a lipophilic moiety, wherein the lipophilic moiety comprises a hydrocarbon having from about 3 to about 41 carbon atoms;
wherein said composition forms a micelle.

29. The method of treating cancer of claims 28, wherein the lipophilic moiety comprises a hydrocarbon having from about 3 to about 41 carbon atoms.

30. The method of treating cancer of claim 28, wherein the lipophilic moiety comprises a hydrocarbon having from about 5 to about 25 carbon atoms.

31. The method of treating cancer of claim 28, wherein the chemotherapeutic agent of the administered composition is a vinca alkaloid, mitomycin-type antibiotic, bleomycin-type antibiotic, antifolate, colchicine, demecoline, etoposide, taxane or anthracycline antibiotic.

32. The method of treating cancer of claim 31, wherein the chemotherapeutic agent of the administered composition is the anthracycline antibiotic doxorubicin, daunorubicin, carminomycin, epirubicin, idarubicin, mithoxantrone, 4-demethoxy-daunomycin, 11-deoxydaunorubicin, 13-deoxydaunorubicin, adriamycin-14-benzoate, adriamycin-14-octanoate or adriamycin-14-naphthaleneacetate.

33. The method of treating cancer of claim 28, wherein the cancer is a leukemia, breast cancer, ovarian cancer, pancreatic cancer, lung cancer, myeloma, melanoma, glioma or astrocytoma.

34. The method of treating cancer of claim 28, wherein the cancer is Hodgkin's lymphoma, non-Hodgkin's lymphoma, acute lymphocytic lymphoma, acute myelocytic lymphoma, acute non-lymphatic leukemia, Karposi's sarcoma, small-cell lung cancer, non-small cell lung cancer or glial astrocytoma.

35. A method of treating a microbial infection of the brain comprising administering to an animal a composition comprising:

(a) a microbially effective amount of a chemotherapeutic agent; and (b) a polyether block copolymer comprising an A-type linear polymeric segment having molecular weight contributions between about 30 and about 500, joined at one end to a B-type linear polymeric segment having molecular weight contributions between about 30 and about 500; and (c) a targeting molecule comprising a targeting moiety and a lipophilic moiety, wherein the lipophilic moiety comprises a hydrocarbon having from about 3 to about 41 carbon atoms;

wherein said composition forms a micelle.

\* \* \* \* \*